US010638923B2

(12) United States Patent
Shirota et al.

(10) Patent No.: US 10,638,923 B2
(45) Date of Patent: *May 5, 2020

(54) COOLING UNIT AND LIGHT SOURCE APPARATUS FOR ENDOSCOPE

(71) Applicant: OLYMPUS CORPORATION, Tokyo (JP)

(72) Inventors: Yutaka Shirota, Hino (JP); Masaaki Watanabe, Hachioji (JP)

(73) Assignee: OLYPMUS CORPORATION, Tokyo (JP)

( * ) Notice: Subject to any disclaimer, the term of this patent is extended or adjusted under 35 U.S.C. 154(b) by 373 days.

This patent is subject to a terminal disclaimer.

(21) Appl. No.: 15/658,457

(22) Filed: Jul. 25, 2017

(65) Prior Publication Data

US 2017/0319056 A1 Nov. 9, 2017

Related U.S. Application Data

(63) Continuation of application No. PCT/JP2016/055454, filed on Feb. 24, 2016.

(30) Foreign Application Priority Data

Apr. 14, 2015 (JP) ................. 2015-082692

(51) Int. Cl.
*A61B 1/00* (2006.01)
*A61B 1/12* (2006.01)
(Continued)

(52) U.S. Cl.
CPC .......... *A61B 1/128* (2013.01); *A61B 1/00117* (2013.01); *A61B 1/00126* (2013.01);
(Continued)

(58) Field of Classification Search
CPC .......... A61B 1/12; A61B 1/125; A61B 1/128; A61B 1/0684; A61B 1/0669; F21V 29/50; F21V 29/502
(Continued)

(56) References Cited

U.S. PATENT DOCUMENTS 5,076,660 A * 12/1991 Messinger ............... A61B 1/07
385/119
2003/0163025 A1 8/2003 Kaji
(Continued)

FOREIGN PATENT DOCUMENTS

CN 1440721 A 9/2003
JP 2007-109853 A 4/2007
(Continued)

OTHER PUBLICATIONS

International Search Report dated May 17, 2016 issued in PCT/JP2016/055454.
(Continued)

*Primary Examiner* — Matthew J Kasztejna
(74) *Attorney, Agent, or Firm* — Scully, Scott, Murphy & Presser, P.C.

(57) ABSTRACT

The cooling unit includes: an opening part through which the cooling media flow in; a first flow path; a second flow path; a first heat generation section; a second heat generation section; a first heat dissipation section that is thermally connected to the first heat generation section, and is disposed in the first flow path; and a second heat dissipation section that is thermally connected to the second heat generation section, and is disposed in the second flow path. The second flow path is disposed between the first and second heat generation sections and the first flow path, and the first heat (Continued)

dissipation section has a thermal resistance value smaller than a thermal resistance value of the second heat dissipation section.

6 Claims, 5 Drawing Sheets

(51) Int. Cl.
    *A61B 1/06*     (2006.01)
    *G02B 23/26*     (2006.01)
    *G02B 7/00*     (2006.01)
    *G02B 27/14*     (2006.01)
    *G02B 23/24*     (2006.01)

(52) U.S. Cl.
    CPC .............. *A61B 1/06* (2013.01); *A61B 1/0669* (2013.01); *A61B 1/0684* (2013.01); *G02B 7/008* (2013.01); *G02B 23/2469* (2013.01); *G02B 23/26* (2013.01); *G02B 27/145* (2013.01)

(58) Field of Classification Search
    USPC ........................................................ 600/178
    See application file for complete search history.

(56) References Cited

U.S. PATENT DOCUMENTS

| | | | |
|---|---|---|---|
| 2009/0076329 A1* | 3/2009 | Su | A61B 1/0008 600/134 |
| 2009/0154192 A1* | 6/2009 | Krattiger | A61B 1/07 362/574 |
| 2013/0146254 A1 | 6/2013 | Jeon et al. | |
| 2016/0126698 A1* | 5/2016 | Nishio | A61B 1/0661 372/34 |
| 2016/0235285 A1* | 8/2016 | Shirota | A61B 1/0638 |
| 2016/0353984 A1* | 12/2016 | Shirota | G02B 23/24 |

FOREIGN PATENT DOCUMENTS

| | | |
|---|---|---|
| JP | 2013-123030 A | 6/2013 |
| JP | 2013-215435 A | 10/2013 |
| JP | 2014-045820 A | 3/2014 |
| WO | WO 2015/178054 A1 | 11/2015 |

OTHER PUBLICATIONS

Japanese Office Action dated Jan. 31, 2017 issued in JP 2016-560605.

* cited by examiner

FIG. 3

|  | RED LED(11a) | GREEN LED(11b) | BLUE LED(11c) | PURPLE LED(11d) |
|---|---|---|---|---|
| WHITE LIGHT MODE | ON | ON | ON | OFF |
| SPECIAL LIGHT MODE | OFF | ON | OFF | ON |

FIG. 4

|  | RED LED(11a) | GREEN LED(11b) | BLUE LED(11c) | PURPLE LED(11d) |
|---|---|---|---|---|
| ALLOWABLE TEMPERATURE RISE AMOUNT[°C] | 50 | 90 | 90 | 90 |
| MAXIMUM HEAT GENERATION AMOUNT[W] | 43.8 | 99 | 47 | 79.2 |
| HEAT DISSIPATION PERFORMANCE INDEX[°C/W] | 1.14 | 0.91 | 1.91 | 1.13 |

COOLING UNIT AND LIGHT SOURCE APPARATUS FOR ENDOSCOPE

CROSS REFERENCE TO RELATED APPLICATION

This application is a continuation application of PCT/JP2016/055454 filed on Feb. 24, 2016 and claims benefit of Japanese Application No. 2015-082692 filed in Japan on Apr. 14, 2015, the entire contents of which are incorporated herein by this reference.

BACKGROUND OF INVENTION

1. Field of the Invention

The present invention relates to a cooling unit that cools a plurality of heat generation sections, and to a light source apparatus for endoscope.

2. Description of the Related Art

For example, as disclosed in Japanese Patent Application Laid-Open Publication No. 2013-215435, a light source apparatus for endoscope that includes a plurality of solid-state light emitting devices such as LEDs and laser diodes, is well-known.

The solid-state light emitting device generates heat when being driven. Therefore, when the solid-state light emitting device is used as a light source in the light source apparatus for endoscope, it is necessary to provide a cooling unit that cools the solid-state light emitting device. As the cooling unit that cools the plurality of solid-state light emitting devices, a configuration in which a plurality of heat dissipation sections such as heatsinks are provided corresponding to the respective solid-state light emitting devices, in a flow path through which an air serving as a cooling medium flows, is considered.

SUMMARY OF THE INVENTION

A cooling unit according to an aspect of the present invention is configured to dissipate heat generated from a plurality of heat generation sections to cooling media by a plurality of heat dissipation sections, and the plurality of heat dissipation sections are provided corresponding to the plurality of heat generation sections respectively. The cooling unit includes: an opening part through which the cooling media flow in; a first flow path that is connected to the opening part to form a space through which a first cooling medium passes, among the cooling media flowing in from the opening part; a second flow path that is connected to the opening part to form a space through which a second cooling medium passes, among the cooling media flowing in from the opening part, the second cooling medium being different from the first cooling medium; a first heat generation section; a second heat generation section; a first heat dissipation section that is thermally connected to the first heat generation section, and is disposed in the first flow path to dissipate heat to the first cooling medium passing through the first flow path; and a second heat dissipation section that is thermally connected to the second heat generation section, and is disposed in the second flow path to dissipate heat to the second cooling medium passing through the second flow path. The second flow path is disposed between the first and second heat generation sections and the first flow path, and the first heat dissipation section has a thermal resistance value smaller than a thermal resistance value of the second heat dissipation section.

In addition, a light source apparatus for endoscope according to an aspect of the present invention includes: the cooling unit; and a plurality of solid-state light emitting devices emitting light of different wavelengths, as the plurality of heat generation sections.

BRIEF DESCRIPTION OF THE DRAWINGS

FIG. 3 is a table to explain operation modes of the light source apparatus for endoscope;

FIG. 4 is a table illustrating thermal characteristics of a plurality of solid-state light-emitting devices provided in the light source apparatus for endoscope;

DETAILED DESCRIPTION OF THE PREFERRED EMBODIMENT(S)

Figure 1:
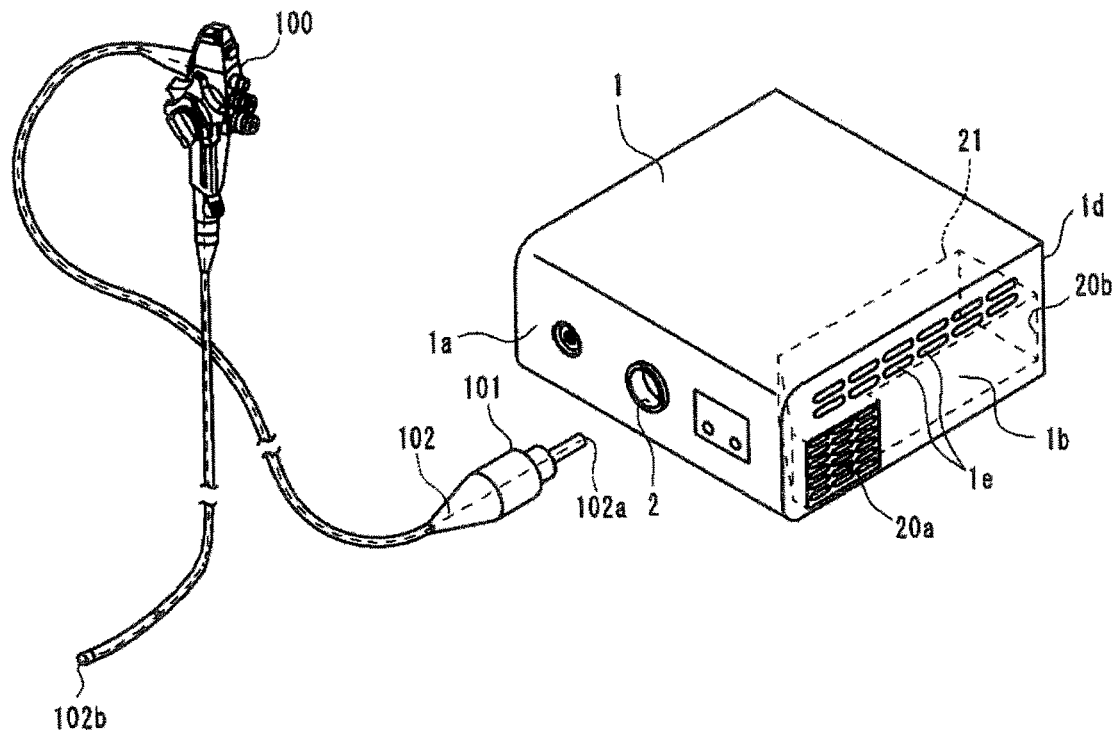
FIG. 1 is a perspective view of a light source apparatus for endoscope.

Some preferred embodiments of the present invention are described below with reference to drawings. Note that, in the drawings used for the following description, scale size is varied for each component in order to illustrate each component with a recognizable size in the drawings. The present invention is not limited only to the number of components, shapes of respective components, a size ratio of components, and relative positional relationship between respective components illustrated in the drawings.

First Embodiment

A light source apparatus 1 for endoscope according to the present embodiment is an apparatus that emits light to illuminate an object observed through an endoscope 100. The endoscope 100 optically picks up an image of a predetermined observation site in a subject such as a human body and in an object such as a structure, and provides the image to an unillustrated display apparatus. The description of the configuration of the endoscope 100 is omitted because the configuration is well-known.

As illustrated in FIG. 1, the light source apparatus 1 for endoscope includes a connector portion 2 that is connected to a plug part 101 provided in the endoscope 100. The connector portion 2 is provided on a front surface 1a of a housing of the light source apparatus 1 for endoscope. A first end part 102a of an optical fiber cable 102 that is inserted into the endoscope 100 is provided at the plug part 101. Light that has entered the first end part 102a of the optical fiber cable 102 is outputted from a second end part 102b toward an object of the endoscope 100.

The light source apparatus 1 for endoscope includes a plurality of solid-state light emitting devices that serve as a plurality of heat generation sections as described later, and causes the light emitted from the solid-state light emitting devices to enter the end part 102a of the optical fiber cable 102 connected to the connector portion 2. The light source apparatus 1 for endoscope includes a cooling unit 20 (not illustrated in FIG. 1) to cool the solid-state light emitting devices. An inlet port 20a and an exhaust port 20b are provided on an external surface of the light source apparatus 1 for endoscope. The inlet port 20a is an opening part to introduce air serving as a cooling medium, into a flow path 21 provided in the cooling unit 20. The exhaust port 20b is an opening part to exhaust the air from the flow path 21. Note that wall surfaces configuring the flow path 21 may be divided into a plurality of plate-like members.

In the present embodiment, the inlet port 20a is provided on a left side surface 1b of the housing of the light source apparatus 1 for endoscope, and the exhaust port 20b is provided on a rear surface 1d of the housing. Note that the respective positions at which the inlet port 20a and the exhaust port 20b are provided are not limited to the positions in the present embodiment. In addition, inlet ports 1e to cool the inside of the housing is provided at an upper part of the left side surface 1b of the housing of the light source apparatus 1 for endoscope.

Figure 2:
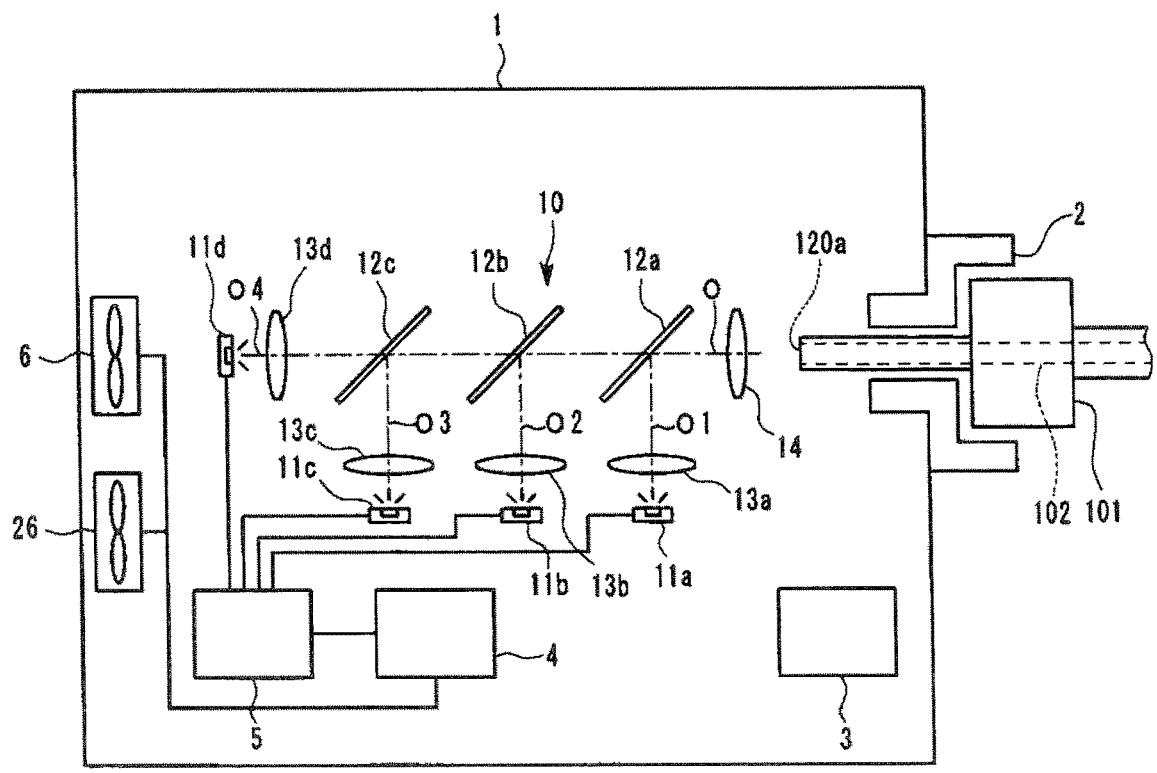
FIG. 2 is a diagram to explain an electric and optical configuration of the light source apparatus for endoscope.

FIG. 2 is a diagram illustrating an electric and optical configuration of the light source apparatus 1 for endoscope. As illustrated in FIG. 2, the light source apparatus 1 for endoscope includes an illumination light emitting unit 10, a power supply section 3, a control section 4, a light source drive section 5, an in-housing cooling fan 6, and a light source cooling fan 26.

The power supply section 3 supplies power to drive respective components configuring the light source apparatus 1 for endoscope. The control section 4 includes a central processing unit (CPU), a memory device (RAM), an auxiliary memory device, an input-output device, and the like, and controls operation of the light source apparatus 1 for endoscope on the basis of predetermined programs. The control section 4 may include an image processing section that performs predetermined image processing on the image picked-up by the endoscope 100 and displays the processed image on an external image display apparatus. The light source drive section 5 includes an electric circuit that drives the solid-state light emitting devices described later in response to instruction from the control section 4.

The illumination light emitting unit 10 includes four solid-state light emitting devices. In the present embodiment, for example, the four solid-state light emitting devices are a red LED 11a, a green LED 11b, a blue LED 11c, and a purple LED 11d that emit light of respective predetermined wavelength ranges with different center wavelengths.

Note that each of the solid-state light emitting devices may be any of a laser diode and a light emitting diode (LED). In addition, a wavelength of the light emitted from each of the solid-state light emitting devices is not particularly limited.

The red LED 11a, the green LED 11b, the blue LED 11c, and the purple LED 11d are electrically connected to the light source drive section 5, and emit light in response to electric signals outputted from the light source drive section 5. Further, intensity of the light emitted from the red LED 11a, the green LED 11b, the blue LED 11c, and the purple LED 11d is varied in response to the electric signals outputted from the light source drive section 5.

The light emitted from the red LED 11a, the green LED 11b, the blue LED 11c, and the purple LED 11d is respectively converted into parallel light by collimator lenses 13a, 13b, 13c, and 13d, and is then led to a condenser lens 14 by dichroic mirrors 12a, 12b, and 12c. The condenser lens 14 condenses the light emitted from the red LED 11a, the green LED 11b, the blue LED 11c, and the purple LED 11d to the end part 102a of the optical fiber cable 102 located at the connector portion 2.

More specifically, in the present embodiment, when an axis passing through a center of the condenser lens 14 is regarded as an optical axis O, the purple LED 11d is provided in the optical axis O, and the red LED 11a, the green LED 11b, and the blue LED 11c are provided at respective positions out of the optical axis O. In other words, the optical axis O is a center axis of the light emitted from the illumination light emitting unit 10.

When the center axes of the light emitted from the red LED 11a, the green LED 11b, the blue LED 11c, and the purple LED 11d are respectively denoted by axes O1, O2, O3, and O4, the axis O4 is parallel to the optical axis O.

In contrast, the red LED 11a, the green LED 11b, and the blue LED 11c are disposed such that the axes O1, O2 and O3 are orthogonal to the optical axis O in one plane including the optical axis O. Further, the red LED 11a, the green LED 11b, and the blue LED 11c are all disposed on one side (a lower side in FIG. 2) with respect to the optical axis O in the one plane including the optical axis O.

The collimator lenses 13a, 13b, 13c, and 13d are respectively disposed in front of the red LED 11a, the green LED 11b, the blue LED 11c, and the purple LED 11d in a light emitting direction, and respectively convert the light received from the red LED 11a, the green LED 11b, the blue LED 11c, and the purple LED 11d into parallel light and output the parallel light.

The dichroic mirrors 12a, 12b, and 12c are respectively provided in front of the three collimator lenses 13a, 13b, and 13c. The dichroic mirrors 12a, 12b, and 12c are arranged along the optical axis O. The dichroic mirrors 12a, 12b, and 12c are provided such that respective reflection surfaces are orthogonal to the plane including the optical axis O and the axes O1, O2, and O3, and the respective reflection surfaces are inclined by 45 degrees to the optical axis O in the plane.

The reflection surface of the dichroic mirror 12a reflects the light of the predetermined wavelength band including the wavelength of the light emitted from the red LED 11a, and allows the light of other wavelength bands to pass through the dichroic mirror 12a. The reflection surface of the dichroic mirror 12b reflects the light of the predetermined wavelength band including the wavelength of the light emitted from the green LED 11b, and allows the light of other wavelength bands to pass through the dichroic mirror 12b. The reflection surface of the dichroic mirror 12c reflects the light of the predetermined wavelength band including the wavelength of the light emitted from the blue LED 11c, and allows the light of other wavelength bands to pass through the dichroic mirror 12c.

The parallel light that has been respectively outputted from the collimator lenses 13a, 13b, and 13c and has been respectively reflected by the dichroic mirrors 12a, 12b, and 12c is combined with the light outputted from the collimator lens 13d, and the combined light enters the condenser lens 14.

In the illumination light emitting unit 10 having the above-described configuration, the red LED 11a, the green LED 11b, the blue LED 11c, and the purple LED 11d are disposed such that the center axes of the respective emitted light are located on one plane. Therefore, the red LED 11a, the green LED 11b, the blue LED 11c, and the purple LED 11d are arranged in order in a predetermined direction along the optical axis O. Moreover, the red LED 11a, the green LED 11b, the blue LED 11c, and the purple LED 11d are so disposed as not to be overlapped with one another in a direction orthogonal to the optical axis O.

Note that the number of the solid-state light emitting devices provided in the illumination light emitting unit 10 is not limited to four as long as two or more.

The light source apparatus 1 for endoscope that includes the illumination light emitting unit 10 having the above-described configuration includes operation modes to cause some of the red LED 11a, the green LED 11b, the blue LED 11c, and the purple LED 11d as the four solid-state light emitting devices, to emit light with different combinations.

More specifically, the light source apparatus 1 for endoscope may carry out two operation modes of a white light mode and a special light mode illustrated in FIG. 3 by switching. In the white light mode, the red LED 11a, the green LED 11b, and the blue LED 11c emit light at the same time. The white light mode is used for normal observation through the endoscope 100. In the special light mode, the green LED 11b and the purple LED 11d emit light at the same time. The special light mode is used for narrow band light observation (narrow band imaging) through the endoscope 100.

Moreover, in the present embodiment, for example, each of the red LED 11a, the green LED 11b, the blue LED 11c, and the purple LED 11d that serve as the plurality of heat generation sections provided in the illumination light emitting unit 10 has thermal characteristic values illustrated in FIG. 4. In a table illustrated in FIG. 4, a temperature rise amount is a difference between temperature allowable for each of the solid-state light emitting devices at maximum light emission and temperature of ambient atmosphere. In addition, a maximum heat generation amount is a heat generation amount at light emission at rating of each of the solid-state light emitting devices.

Although detail is described later, the heat dissipation section serving as a heatsink cools the solid-state light emitting device serving as the heat generation section. A heat dissipation performance index is a value calculated by dividing the temperature rise amount by the maximum heat generation amount. The heat dissipation performance index is a value of a thermal resistance of the solid-state light emitting device and the heat dissipation section with the ambient atmosphere, necessary to maintain the temperature of each of the solid-state light emitting devices to the value of the temperature rise amount when each of the solid-state light emitting devices emit light at rating.

In other words, the value of the heat dissipation performance index becomes a reference to calculate the thermal resistance necessary for the heat dissipation section. For example, the heat dissipation section having a smaller thermal resistance value is necessary as the value of the heat dissipation performance index of the solid-state light emitting device is smaller. It is possible to reduce the thermal resistance value of the heat dissipation section by, for example, increasing a surface area of the heat dissipation section.

As illustrated in FIG. 4, in the present embodiment, the value of the heat dissipation performance index of the green LED 11b is the smallest, and the value of the heat dissipation performance index becomes larger in order of the purple LED 11d, the red LED 11a, and the blue LED 11c.

In other words, among the three solid-state light emitting devices that emit light at the same time in the white light mode, the value of the heat dissipation performance index of the green LED 11b is the smallest, and the value of the heat dissipation performance index becomes larger in order of the red LED 11a and the blue LED 11c. In addition, between the two solid-state light emitting devices that emit light at the same time in the special light mode, the value of the heat dissipation performance index of the green LED 11b is the smallest.

The in-housing cooling fan 6 is an electric fan that exhausts the air inside the housing of the light source apparatus 1 for endoscope. Note that a plurality of in-housing cooling fans 6 may be provided.

The light source cooling fan 26 is an electric fan provided in the cooling unit 20 described later. A rotation speed of the light source cooling fan 26 is controlled by the control section 4. The light source cooling fan 26 may be provided singularly or two or more light source cooling fans 26 may be provided.

Figure 5:
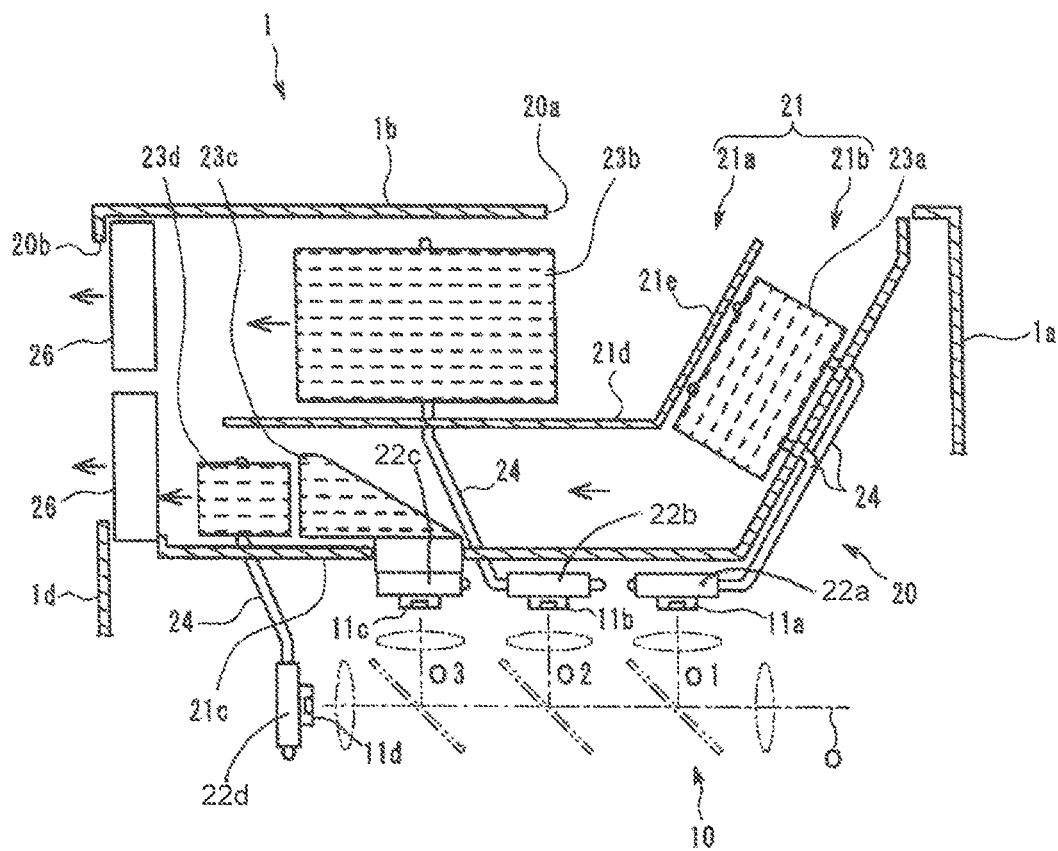
FIG. 5 is a diagram to explain a configuration of a cooling unit.

FIG. 5 is a diagram illustrating a configuration of the cooling unit 20. FIG. 5 is a diagram illustrating the cooling unit 20 as viewed from an upper side of the light source apparatus 1 for endoscope. In FIG. 5, right side in the figure corresponds to front side of the light source apparatus 1 for endoscope, and upper side in the figure corresponds to left side of the light source apparatus 1 for endoscope.

As illustrated in FIG. 5, the illumination light emitting unit 10 is disposed such that the optical axis O extends in parallel to a front-rear direction of the light source apparatus 1 for endoscope and the axes O1, O2, and O3 become substantially horizontal. Further, the red LED 11a, the green LED 11b, and the blue LED 11c are disposed on side close to the left side surface 1b of the housing with respect to the optical axis O.

The cooling unit 20 is disposed between the illumination light emitting unit 10 and the left side surface 1b of the housing. The cooling unit 20 cools the red LED 11a, the green LED 11b, the blue LED 11c, and the purple LED 11d that serve as the plurality of heat generation sections provided in the illumination light emitting unit 10.

The cooling unit 20 includes a plurality of heat receiving sections to which heat generated by the plurality of heat generation sections is transferred and a plurality of heat dissipation sections to which heat is transferred from the plurality of heat receiving sections, and dissipates heat from the plurality of heat dissipation sections to the air serving as a cooling medium. The plurality of heat dissipation sections are disposed in a flow path through which the air forcibly flows.

More specifically, a plurality of heat receiving sections 22a, 22b, 22c, and 22d are respectively provided near the red LED 11a, the green LED 11b, the blue LED 11c, and the purple LED 11d that serve as the plurality of heat generation sections. The plurality of heat receiving sections 22a, 22b, 22c, and 22d are members to which the heat generated by the red LED 11a, the green LED 11b, the blue LED 11c, and the purple LED 11d are respectively transferred. Note that the heat receiving sections 22a, 22b, 22c, and 22d and the red LED 11a, the green LED 11b, the blue LED 11c, and the purple LED 11d may be respectively in direct contact with each other, or may be respectively in contact with each other with a heat transfer member in between.

The flow path 21 is a site through which the air serving as the cooling medium passes. One end of the flow path 21 is connected to the inlet port 20a provided on the left side surface 1b of the housing of the light source apparatus 1 for endoscope, and the other end of the flow path 21 is connected to the exhaust port 20b provided on the rear surface 1d of the housing of the light source apparatus 1 for endoscope.

In the present embodiment, for example, operation of the light source cooling fan 26 that is the electric fan forcibly causes the air serving as the cooling medium to flow in the flow path 21. In the present embodiment, the light source cooling fan 26 is disposed near the exhaust port 20b. The light source cooling fan 26, however, may be disposed near the inlet port 20a or near both of the inlet port 20a and the exhaust port 20b.

The air flows in a direction from the inlet port 20a toward the exhaust port 20b in the flow path 21 by operation of the light source cooling fan 26. In other words, in the flow path 21, a direction approaching the inlet port 20a is an upstream side of the flow of the air in the flow path 21, and a direction approaching the exhaust port 20b is a downstream side.

The flow path 21 is divided into two flow paths of a first flow path 21a and a second flow path 21b that are substantially parallel to each other. In the present embodiment, for example, a partition plate 21d is disposed in the flow path 21 to form the two flow paths of the first flow path 21a and the second flow path 21b. The first flow path 21a has a cross-sectional area larger than a cross-sectional area of the second flow path 21b.

The first flow path 21a is so disposed as to sandwich the second flow path 21b between the heat receiving sections 22a, 22b, 22c and 22d and the first flow path 21a. In other words, the second flow path 21b is close to the red LED 11a, the green LED 11b, the blue LED 11c, and the purple LED 11d that serve as the plurality of heat generation sections, and the first flow path 21a is disposed along the left side surface 1b of the housing of the light source apparatus 1 for endoscope, at a position separated from the heat generation sections than the second flow path 21b.

An upstream end part 21e of the partition plate 21d is so inclined, inside the housing of the inlet port 20a, by a predetermined angle to an opening direction of the inlet port 20a as to come close to the rear surface 1d of the housing, from the inlet port 20a toward the inside of the housing. A direction of the flow of the air that flows from the inlet port 20a into the first flow path 21a is changed by the upstream end part 21e of the partition plate 21d such that the air flows along the side surface 1b of the housing toward the rear surface 1d of the housing. This makes it possible to uniformize distribution of flow rate of the air in the cross-sectional surface direction inside the first flow path 21a.

The plurality of heat dissipation sections 23a, 23b, 23c, and 23d that serve as heatsinks provided respectively corresponding to the plurality of heat receiving sections 22a, 22b, 22c, and 22d are disposed in the flow path 21. The heat from the plurality of heat receiving sections 22a, 22b, 22c, and 22d is respectively transferred to the plurality of heat dissipation sections 23a, 23b, 23c, and 23d through a heat transfer section 24 such as a heat pipe or direct contact with the plurality of heat receiving sections 22a, 22b, 22c, and 22d.

Placement of the plurality of heat dissipation sections 23a, 23b, 23c, and 23d in the flow path 21 is described below.

In the present embodiment, a first heat dissipation section that cools the solid-state light emitting device (a first heat generation section) having a smallest value of the heat dissipation performance index among the solid-state light emitting devices emitting light at the same time, is disposed singularly in the first flow path 21a. In addition, a second heat dissipation section that cools the solid-state light emitting device (a second heat generation section) having a second smallest value of the heat dissipation performance index among the solid-state light emitting devices emitting light at the same time, is disposed in the second flow path 21b. Further, a third heat dissipation section that cools a remaining solid-state light emitting device (a third heat generation section) is disposed on a downstream side of the second heat dissipation section in the second flow path 21b.

As mentioned above, in the present embodiment, the red LED 11a, the green LED 11b, and the blue LED 11c emit light at the same time in the white light mode. In other words, since the purple LED 11d does not emit light in the white light mode, the purple LED 11d is not included in the heat generation sections.

Among the solid-state light emitting devices emitting light at the same time in the white light mode, the solid-state light emitting device (the first heat generation section) having the smallest value of the heat dissipation performance index is the green LED 11b. In addition, among the solid-state light emitting devices emitting light at the same time in the white light mode, the solid-state light emitting device (the second heat generation section) having the second smallest value of the heat dissipation performance index is the red LED 11a. Further, in the white light mode, the solid-state light emitting device (the third heat generation section) having a value of the heat dissipation performance index larger than the value of the heat dissipation performance index of the red LED 11a is the blue LED 11c.

Accordingly, as illustrated in FIG. 5, the heat dissipation section 23b (the first heat dissipation section) that cools the green LED 11b is singularly disposed in the first flow path 21a. In addition, the heat dissipation section 23a (the second heat dissipation section) that cools the red LED 11a is disposed in the second flow path 21b. Further, the heat dissipation section 23c (the third heat dissipation section) that cools the blue LED 11c is disposed on the downstream side of the heat dissipation section 23a in the second flow path 21b. In other words, the heat dissipation section 23a and the heat dissipation section 23c are disposed in order from the upstream toward the downstream in the second flow path 21b.

In the special light mode, the green LED 11b and the purple LED 11d emit light at the same time. In other words, in the special light mode, the green LED 11b and the purple LED 11d correspond to the plurality of heat generation sections, and the red LED 11a and the blue LED 11c are not included in the heat generation sections because the red LED 11a and the blue LED 11c do not emit light.

Among the solid-state light emitting devices emitting light at the same time in the special light mode, the solid-state light emitting device (the first heat generation section) having the smallest value of the heat dissipation performance index is the green LED 11b. In addition, among the solid-state light emitting devices emitting light at the same time in the special light mode, the solid-state light emitting device (the second heat generation section) having the second smallest value of the heat dissipation performance index is the purple LED 11d.

As illustrated in FIG. 5, the heat dissipation section 23b (the first heat dissipation section) that cools the green LED 11b is singularly disposed in the first flow path 21a, as described for the white light mode. Further, the heat dissipation section 23d (the second heat dissipation section) that cools the purple LED 11d is disposed in the second flow path 21b. Here, since the heat dissipation sections 23a and 23c do not perform heat dissipation in the special light mode, the heat dissipation section 23d that cools the purple LED 11d is located at the most upstream among the heat dissipation sections in the second flow path 21b irrespective of the location of the heat dissipation section 23d in the second flow path 21b.

In the cooling unit 20 having the above-described configuration, the light source cooling fan 26 is operated to cause the air at the predetermined flow rate to flow through the flow path 21, which makes it possible to dissipate, to the air, the heat that has been transferred from the plurality of heat receiving sections 22a, 22b, 22c, and 22d to the plurality of heat dissipation sections 23a, 23b, 23c, and 23d. In other words, the cooling unit 20 makes it possible to cool the red LED 11a, the green LED 11b, the blue LED 11c, and the purple LED 11d that serve as the plurality of heat generation sections.

Here, in the cooling unit 20 according to the present embodiment, the flow path 21 through which the air serving as the cooling medium flows is divided into the first flow path 21a and the second flow path 21b. In the first flow path 21a, the first heat dissipation section 23b provided corresponding to the green LED 11b that requires a heat dissipation section having a small thermal resistance value, is singularly disposed. In the second flow path 21b, the second heat dissipation sections 23a and 23d provided respectively corresponding to the red LED 11a and the purple LED 11d that require a heat dissipation section having a next small thermal resistance value to the green LED 11b, are disposed.

As mentioned above, in the present embodiment, since the air flowing through the different flow paths are applied to the first heat dissipation section and the second heat dissipation section, it is possible to prevent thermal interference between the first heat dissipation section and the second heat dissipation section, thereby improving cooling efficiency. Moreover, in the present embodiment, the first heat dissipation section 23b is singularly disposed in the first flow path 21a that is provided separately from the plurality of solid-state light emitting devices generating heat, which makes it possible to further improve the cooling efficiency of the first heat dissipation section 23b.

Furthermore, in the present embodiment, the second heat dissipation section 23a is located at the most upstream side among the plurality of heat dissipation sections disposed in the second flow path 21b, in the white light mode. Likewise, the second heat dissipation section 23d is also located at the most upstream side in the second flow path 21b, in the special light mode. This makes it possible to apply the air of the low temperature to the second heat dissipation section, thereby improving the cooling efficiency of the second heat dissipation section, in the present embodiment.

As mentioned above, the cooling unit 20 according to the present embodiment is high in cooling efficiency and is downsizable. Therefore, it is possible to downsize the light source apparatus 1 for endoscope including the cooling unit 20 according to the present embodiment.

Second Embodiment

Next, a second embodiment of the present invention is described. In the following, difference with the first embodiment is only described, and components similar to the components of the first embodiment are denoted by the same reference numerals, and description of such components is appropriately omitted.

Figure 6:
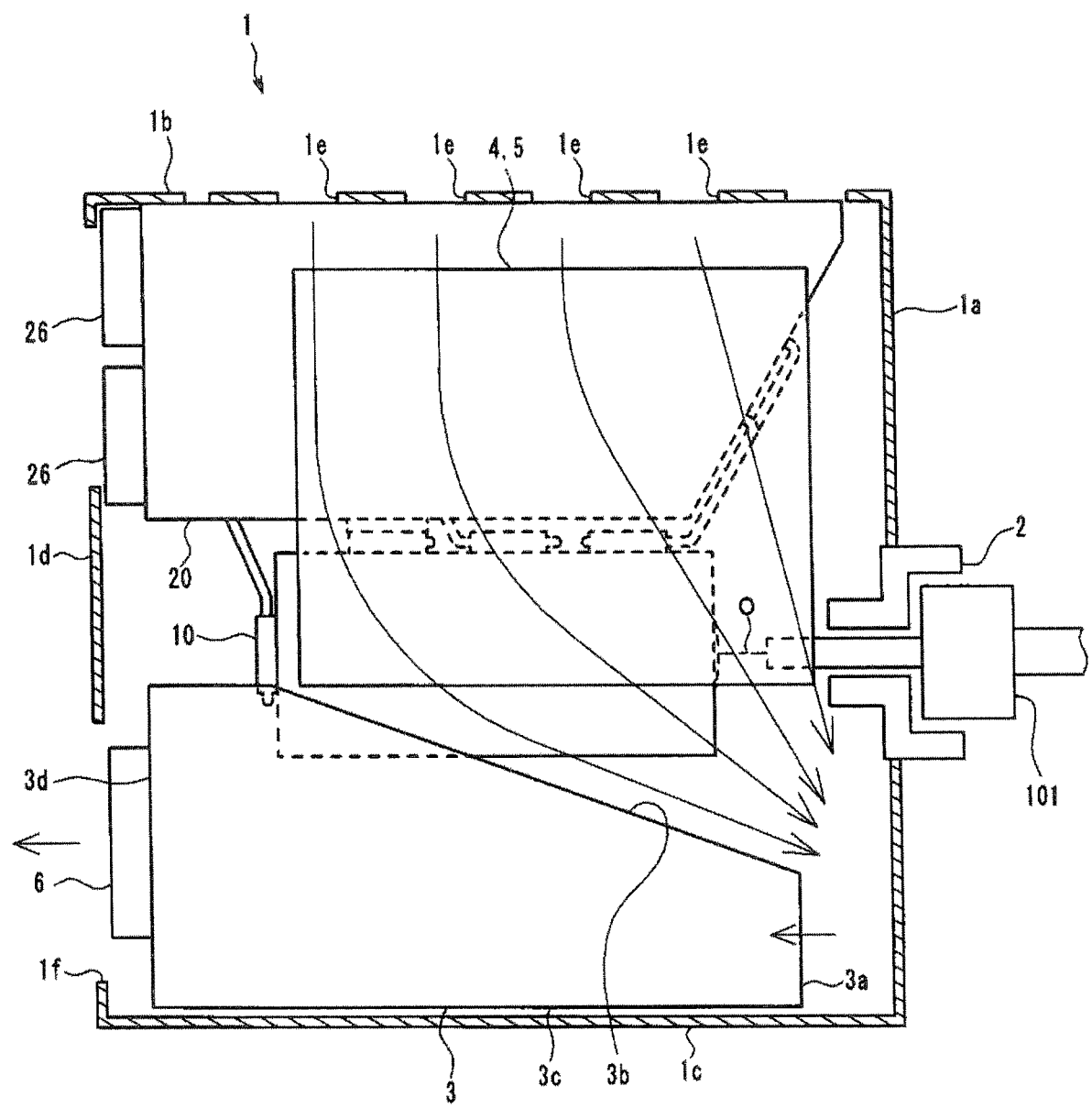
FIG. 6 is a diagram illustrating an inside of a housing of a light source apparatus for endoscope according to a second embodiment.

FIG. 6 is a diagram illustrating placement of the power supply section 3, the control section 4, and the light source drive section 5 inside the housing of the light source apparatus 1 for endoscope. FIG. 6 is a diagram illustrating the inside of the housing of the light source apparatus 1 for endoscope as viewed from the upper side.

As illustrated in FIG. 6, the power supply section 3 is disposed at the right side (the lower side in FIG. 6) of the illumination light emitting unit 10. The power supply section 3 has a box-like outer shape, and includes a power supply circuit. The outer shape of the power supply section 3 includes a front surface 3a, a right side surface 3c, and a rear surface 3d that are respectively substantially parallel to the front surface 1a, the right side surface 1c, and the rear surface 1d of the housing of the light source apparatus 1 for endoscope. In addition, a left side surface 3b of the outer shape of the power supply section 3 is so inclined with respect to the right side surface 3c as to come close to the right side surface 3c toward the front side. In other words, a width of the power supply section 3 in a lateral direction is gradually decreased toward the front side as viewed from the upper side of the power supply section 3.

An air intake opening part is provided on the front surface of the power supply section 3. In addition, an air exhaust opening part and the in-housing cooling fan 6 disposed in the opening part are provided on the rear surface 3d of the power supply section 3.

One or a plurality of electronic circuit substrates configuring the control section 4 and the light source drive section 5 are disposed on the upper side of the illumination light emitting unit 10 and the cooling unit 20. In other words, the control section 4 and the light source drive section 5 are disposed between the left side surface 3b of the power supply section 3 and the left side surface 1b of the housing of the light source apparatus 1 for endoscope.

As illustrated in FIG. 1 and FIG. 6, the plurality of inlet ports 1e through which the air is taken into the housing are arranged on the upper part of the left side surface 1b of the housing in the front-rear direction of the entire housing.

When the in-housing cooling fan 6 is operated, pressure inside the power supply section 3 becomes negative, and pressure inside the housing that communicates with the power supply section 3 also becomes negative. This causes external air to be taken into the housing through the inlet ports 1e of the left side surface 1b of the housing.

The air taken into the housing through the inlet ports 1e flows along a top surface and a bottom surface of the control section 4 and the light source drive section 5 as illustrated by arrows in FIG. 6 to cool the control section 4 and the light source drive section 5, and then passes through the opening parts provided on the front surface 3a and the left side surface 3b of the power supply section 3, thereby flowing into the power supply section 3. Here, since the left side surface 3b of the outer shape of the power supply section 3 that faces the control section 4 and the light source drive section 5 is so inclined as to be away from the inlet ports 1e toward the front side, the air is guided by the left side surface 3b and so smoothly flow as to be collected to the front surface 3a of the power supply section 3. Accordingly, in the present embodiment, it is possible to improve the cooling efficiency of the control section 4 and the light source drive section 5 without unevenness in the flow of the air cooling the control section 4 and the light source drive section 5.

Further, the air that has flowed into the power supply section 3 from the front surface 3a of the power supply section 3 cools the inside of the power supply section 3, and the air is then exhausted through an exhaust port 1f on the rear surface 1d of the housing. As mentioned above, in the present embodiment, the in-housing cooling fan 6 provided in the power supply section 3 cools the power supply section 3, the control section 4, and the light source drive section 5. Incidentally, the temperature on the rear surface side of the housing is increased by the air exhausted from the rear surface of the housing. Therefore, the solid-state light emitting devices that are deteriorated by heat are preferably disposed on the front surface side of the housing. Disposing the devices that are easily deteriorated by temperature, among the solid-state light emitting devices, on the front surface side of the housing makes it possible to further improve the cooling efficiency.

Third Embodiment

Next, a third embodiment of the present invention is described. In the following, difference with the first embodiment is only described, and components similar to the components of the first embodiment are denoted by the same reference numerals, and description of such components is appropriately omitted.

Figure 7:
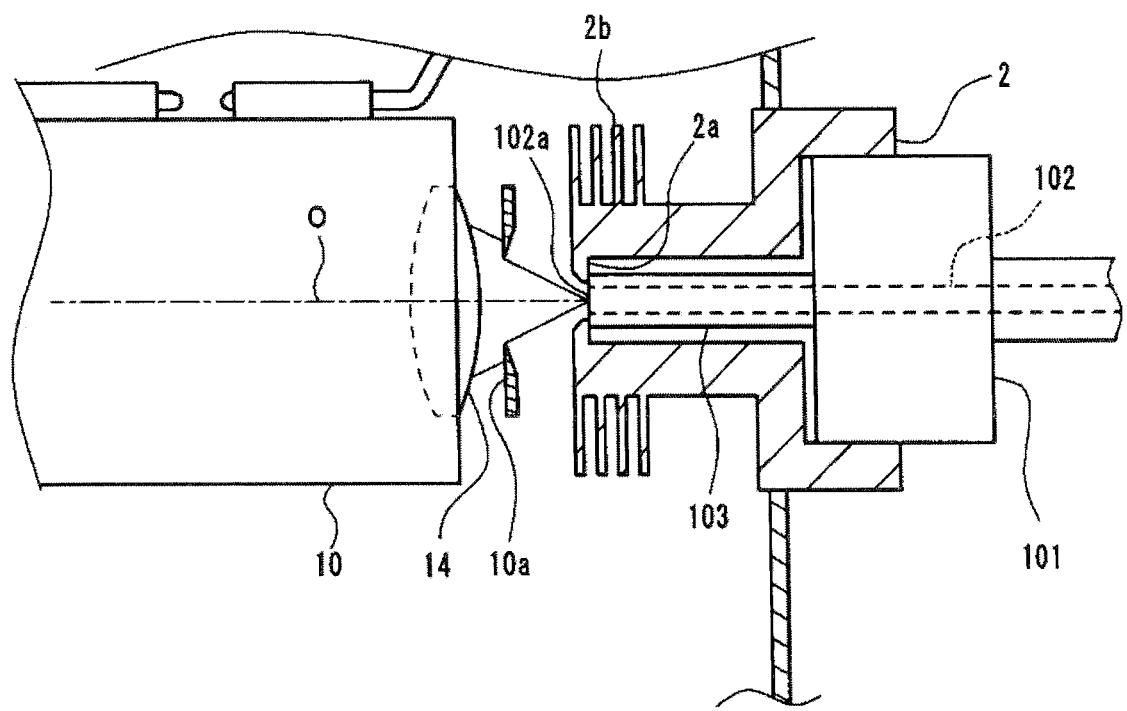
FIG. 7 is a cross-sectional diagram illustrating a vicinity of a connector portion of a light source apparatus for endoscope according to a third embodiment.

FIG. 7 is a cross-sectional diagram illustrating a vicinity of the connector portion 2 of the light source apparatus 1 for endoscope. As illustrated in FIG. 7, the connector portion 2 holds the plug part 101 of the endoscope 100 such that the first end part 102a of the optical fiber cable 102 is located near a focal point of the condenser lens 104 of the illumination light emitting unit 10 in a state where the plug part 101 is inserted into the connector portion 2.

An outer peripheral part in the vicinity of the first end part 102a of the optical fiber cable 102 is covered with a cylindrical pipe sleeve 103. The connector portion 2 includes a pipe sleeve contact part 2a with which an end surface of the pipe sleeve 103 comes into contact. When the end surface of the pipe sleeve 103 comes into contact with the pipe sleeve contact part 2a, the optical fiber cable 102 is positioned with respect to the condenser lens 104.

When the illumination light emitted from the illumination light emitting unit 10 is applied to the pipe sleeve 103, the pipe sleeve 103 is heated. Therefore, in the present embodiment, a heatsink 2b is provided on an outer peripheral surface of a member including the pipe sleeve contact part 2a. Since the pipe sleeve contact part 2a is a member coming into contact with the pipe sleeve 103, the heat of the pipe sleeve 103 that has been heated by the illumination light is dissipated to the air inside the housing through the heatsink 2b of the pipe sleeve contact part 2a. As a result, in the present embodiment, it is possible to prevent temperature increase of the pipe sleeve 103. Note that the heatsink 2b is provided with a fin that is parallel to the vertical direction of the housing in order to prompt cooling by natural convection of the air inside the housing. Further, to facilitate the flow of the air into the heatsink 2b, a portion on bottom surface side of the housing may preferably have a tapered R shape.

In addition, in the present embodiment, an aperture 10a is provided in front of the condenser lens 104 in order to prevent temperature increase of the pipe sleeve 103 caused by the applied illumination light. The aperture 10a is provided such that the illumination light enters only the first end part 102a of the optical fiber cable 102 and the illumination light is not applied to the pipe sleeve 103 provided on the outer periphery of the optical fiber cable 102.

As mentioned above, in the present embodiment, it is possible to prevent temperature increase of the pipe sleeve 103 provided in the plug part 101 of the endoscope 100.

Note that the present invention is not limited to the above-described embodiments. The present invention may be appropriately modified without departing from the essence or spirit of the invention that can be read from the claims and the entire specification, and a cooling unit and a light source apparatus for endoscope which involve such modifications are also intended to be within the technical scope of the present invention.

What is claimed is:

1. A cooling unit that is configured to dissipate heat generated from a plurality of heat sources to a cooling medium by a plurality of heat sinks, the plurality of heat sinks being provided corresponding to the plurality of heat sources, respectively, respectively, the cooling unit comprising:
an opening through which the cooling medium flows in;
a first flow path that is connected to the opening to form a first space through which the cooling medium flowing in from the opening passes;
a second flow path that is connected to the opening to form a second space through which the cooling medium flowing in from the opening passes;
the plurality of heat sources comprising:
a first heat source; and
a second heat source;
the plurality of heat sinks comprising:
a first heat sink thermally connected to the first heat source, the first heat sink being disposed in the first flow path to dissipate heat to the cooling medium passing through the first flow path; and
a second heat sink thermally connected to the second heat source, the second heat sink being disposed in the second flow path to dissipate heat to the cooling medium passing through the second flow path, wherein
the second flow path is disposed between the first and second heat sources and the first flow path, and
the first heat sink has a thermal resistance value smaller than a thermal resistance value of the second heat sink.

2. The cooling unit according to claim 1, wherein
a value determined by dividing a temperature rise amount by a maximum heat generation amount of a heat source at maximum heat generation, is used as a heat dissipation performance index, and
the first heat source has a value of the heat dissipation performance index smaller than a value of the heat dissipation performance index of the second heat sink.

3. The cooling unit according to claim 2, wherein:
the plurality of heat sources further comprises a third heat source having a value of the heat dissipation performance index larger than a value of the heat dissipation performance index of the second heat source; and
the plurality of heat sinks further comprises a third heat sink thermally connected to the third heat source, the third heat sink being disposed on a downstream side of the second heat sink in a flow of the cooling medium inside the second flow path.

4. The cooling unit according to claim 2, wherein the first heat sink has a surface area larger than a surface area of the second heat sink.

5. The cooling unit according to claim 1, wherein the first heat source has a value of the maximum heat generation amount larger than a value of the maximum heat generation amount of the second heat source.

6. A light source apparatus for endoscope, the light source apparatus comprising:
the cooling unit according to claim 1;
wherein the plurality of heat sources comprise a plurality of solid-state light emitting devices emitting light of different wavelengths.

* * * * *

UNITED STATES PATENT AND TRADEMARK OFFICE
CERTIFICATE OF CORRECTION

PATENT NO. : 10,638,923 B2
APPLICATION NO. : 15/658457
DATED : May 5, 2020
INVENTOR(S) : Yutaka Shirota et al.

It is certified that error appears in the above-identified patent and that said Letters Patent is hereby corrected as shown below:

In the Claims

Column 12, Claim 1, Line 8 should read:
sources, respectively, the cooling unit compris- Signed and Sealed this
Thirteenth Day of October, 2020

Andrei Iancu
*Director of the United States Patent and Trademark Office*